United States Patent [19]

Bardos et al.

[11] Patent Number: 4,468,384

[45] Date of Patent: Aug. 28, 1984

[54] METHOD FOR THE INHIBITION OF THE REPLICATION OF DNA VIRUSES WITH 5-SUBSTITUTED 2-PYRIMIDINONE NUCLEOSIDES

[75] Inventors: Thomas J. Bardos, Snyder, N.Y.; Yung-Chi Cheng, Chapel Hill, N.C.; Alan C. Schroeder, Buffalo, N.Y.

[73] Assignee: The Research Foundation of State University of New York, Albany, N.Y.

[21] Appl. No.: 337,297

[22] Filed: Jan. 5, 1982

[51] Int. Cl.[3] .................... A61K 31/70; A61K 39/245
[52] U.S. Cl. ..................................... 424/180; 536/23; 536/29; 424/89
[58] Field of Search .................... 536/23, 29; 424/180, 424/89

[56] References Cited

FOREIGN PATENT DOCUMENTS 134429  2/1979  German Democratic Rep. .

OTHER PUBLICATIONS

Schroeder, A., "Synthesis of New Nucleoside Analogs Derived From 4-Deoxyuracil and 6-Substituted Uracils", A Dissertation Submitted to the Faculty of the Graduate School, State University of New York, 1978.
Cheng, Y. et al., Antimicrobial Agents and Chemotherapy, vol. 10, pp. 119-122, 1976.
Rada, B. et al., Chemotherapy, vol. 20, pp. 141-147, 1974.
Chemical Abstracts, vol. 93, p. 706, Abstract No. 186752v, 1980.
Chemical Abstracts, vol. 81, p. 70, Abstract No. 146282n, 1974.
Chemical Abstracts, vol. 79, p. 136, Abstract No. 144106t, 1973.
Chemical Abstracts, vol. 71, p. 36602c, Abstract No. 36602c, 1969.
Schroeder et al., J. Med. Chem., vol. 24, pp. 109-112, 1980.
Cheng, Y., Federation of European Biochemical Societies Symposia, vol. 57, pp. 263-273, 1978.
De Clercq, E. et al., Federation of European Biochemical Societies Symposia, vol. 57, pp. 275-285, 1978.
Prusoff, W., Federation of European Biochemical Societies Symposia, vol. 57, pp. 287-293, 1978.
Oyen et al., "5-Fluoropyrimidin-2-one Deoxyriboside and its Growth-Inhibiting Properties", Biochim. Biophys. Acta, 182 (1969), pp. 567-569.
Votruba, I. et al., "Mechanism of Inhibition of DNA Synthesis in Escherichia coli by Pyrimidin-2-one β-D-Ribofuranoside", Biochimica et Biophysica Acta, 324 (1973), pp. 14-23.
Laland, S. G. et al., "Synthesis of Pyrimidin-2-one Deoxyribosides and their Ability to Support the Growth of the Deoxyriboside-Requiring Organism Lactobacillus acidophilus R26", Biochem. Journal, 90 (1964), pp. 76-81.
Oyen, T. B., "Synthesis and Properties of Ribosyl-pyrimidin-2-One", Biochimica et Biophysica Acta, 186 (1969), pp. 237-243.
Oftebro, R. et al., "5-Fluoropyrimidin-2-one, A New Metaphase Arresting Agent", Biochemical Pharmacology, 21 (1972), pp. 2451-2456.
McCormack et al., "Inhibition of Cytidine Deaminase by 2-oxopyrimidine Riboside and Related Compounds", Biochemical Pharmacology, 29 (1980), pp. 830-832.
Torrence, P. F. et al., "Synthesis and Antiviral Activities of New 5-Substituted Pyrimidine Nucleoside Analogs", Frontiers in Bioorganic Chemistry and Molecular Biology, (1979), pp. 59-85.
Johns et al., "Enzymic Hydroxylation of 5-Fluoropyrimidines by Aldehyde Oxidase and Xanthine Oxidase", Biochemical Pharmacology, 15 (1966), pp. 400-403.
Prusoff, W. H. et al., "Antiviral Iodinated Pyrimidine Deoxyribonucleosides: 5-IODO-2'-Deoxyuridine; 5 IODO-2'-Deoxycytidine; 5-IODO-5'-Amino-2',-5'-Dideoxyuridine", Pharmaceutical Therapy, 7 (1979), pp. 1-34.
Renis, H. E., "Pyrimidines and Their Nucleosides", Antibiotics Chemotherapy, 27 (1980), pp. 164-207.
Wightman, R. et al., "Nucleic Acid Components and Their Analogues Clix. Synthesis of Some 2-Pyrimidone Nucleosides", Collection of Czechoslov. Chemical Communications, 38 (1973), pp. 1381-1397.
Kohler, P. et al., "Anomeric (1-(2-Deoxy-D-Erythro-Pentofuranosyl)-2(1H)-Pyrimidinones, Nucleic Acid Chemistry, John Wiley & Sons, N.Y. (1978), pp. 283-289.
Johns, D. G., "Human Liver Aldehyde Oxidase: Differential Inhibition of Oxidation of Charged and Uncharged Substrates", Journal of Clinical Investigation, 46 (1967), No. 9, pp. 1492-1505.
Helgeland et al., "The Synthesis, Characterization and Biological Properties of a New Substance, 5-Fluoropyrimidin-2-one", Biochim. Biophys. Acta, 87 (1964), pp. 353-355.
Oyen, T. B. et al., "Preparation and Biological Properties of Deoxyribosides and Deoxyribotides of Pyrimidin-2-one", Biochem. Journal 92 (1964), pp. 27P-28P.
Doskocil et al., "Inhibition of Nucleoside-Binding Sites by Nucleoside Analogues in Escherichia coli", Nucleic Acids Research, (1974), pp. 491-502.
Cheng et al., "Properties of Herpesvirus-Specific Thymidine Kinase, DNA Polymerase and DNase and Their Implication in the Development of Specific Antiherpes Agents", Advances in Ophthalmalogy, 38 (1979), pp. 183-186.
Prusoff et al., "Role of Nucleosides in Virus and Cancer Chemotherapy", Advances in Opthalmalogy, 38 (1079), pp. 3-16.
Nakayama, C. et al., "Synthetic Nucleosides and Nucleotides. XII.[1] Synthesis and Antiviral Activities of Several 1-β-D-Arabinofuranosyl-5-Alkyluracils and Their Monophosphates", Carbohydrates-Nucleosides-Nucleotides, Marcel Dekker, Inc., 6(4), pp. 295-308.
Sakata, S. et al., "Synthesis and Antiherpesviral Activity of 5-C-Substituted Uracil Nucleosides", *Nucleic Acids Research*, 8 (1980), pp. 39–42.

*Primary Examiner*—Blondel Hazel
*Attorney, Agent, or Firm*—Howard M. Ellis; Michael L. Dunn

[57] ABSTRACT

A method for inhibiting the replication of a DNA virus which induces formation of thymidine kinase enzyme, by exposing the virus to an effective concentration of a compound of the formula:

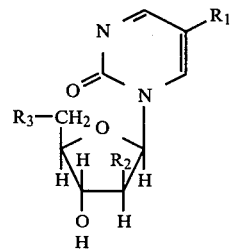

wherein $R_1$ is a radical selected from the group consisting of halogen, $-SCH_3$, $-OH$, alkoxy, cyano, methylamino, carboxy, formyl, nitro and unsubstituted or halosubstituted hydrocarbon groups of 1 through 3 carbon atoms; $R_2$ is hydrogen; halogen or hydroxy; and $R_3$ is hydroxy, $-OP(O)(OH)_2$, amino, or $-OOR_4$ where $R_4$ is lower alkyl of 1 through 6 carbon atoms.

9 Claims, No Drawings

METHOD FOR THE INHIBITION OF THE REPLICATION OF DNA VIRUSES WITH 5-SUBSTITUTED 2-PYRIMIDINONE NUCLEOSIDES

BACKGROUND OF THE INVENTION (A) Field of the Invention

This invention relates to a method for inhibiting the replication of DNA viruses and more particularly relates to a method for inhibiting the replication of DNA viruses which induce the formation of thymidine kinase enzyme.

(B) History of the Prior Art

Historically, viruses have been the causative agents of many diseases of both plants and animals including man. Diseases caused by viruses have been very difficult to control or cure by traditional methods. Many such viral diseases have been, in the past, effectively controlled through mass vaccination but even in modern times, effective agents to cure viral diseases, rather then prevent them, have been unavailable.

It has recently been discovered that certain substituted naturally occurring pyrimidinones are effective antiviral agents. Most of such compounds are 5-substituted pyrimidinones attached to a pentose sugar group at the one position of the pyrimidinone ring. Examples of such compounds and their effects are discussed in "Molecular Basis for Serendipitous Development of Antiviral and Anticancer Aminonucleosides" by Prusofff et al; "Comparative Study of the Potency and Selectivity of Anti-Herpes Compounds" by DeClercq and "Strategy for the Development of Selective Anti-Herpes Virus Agents Based on the Unique Properties of Viral Induced Enzymes—Thymidine Kinase, DNase and DNA Polymerase". All of these articles appear in Volume 57 of a Symposium of the Federation of European Biochemical Sciences, Antimetabolites in Biochemistry, Biology and Medicine edited by Skoda et al, published by Pergamon Press (1978).

Unfortunately, such antiviral compounds, based upon naturally occurring pyrimidinones have a serious disadvantage in that these compounds are rapidly metabolized, generally having a metabolic half life of less than 30 minutes. Such short metabolic life has not permitted such compounds to be effectively used under In Vivo conditions.

Certain compounds, based upon 4-Deoxo uracil have recently been synthesized by two of the inventors herein and presented in a thesis by Alan Curtis Schroeder in 1978.

Such thesis does not in general discuss or suggest any antiviral activity by 5 substituted 4-Deoxo uracil compounds except on page 98 of the thesis wherein it was indicated that such compounds would be tested against Herpes Virus in mouse L cells. There was no indication that such compounds would in fact have any effect after such tests.

BRIEF DESCRIPTION OF THE INVENTION

In accordance with the invention, there is provided a method for inhibiting the replication of the DNA virus which induces formation of thymidine kinase enzyme. In accordance with the method, the virus is exposed to an effective concentration of the compound of the formula:

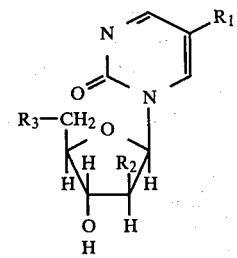

wherein $R_1$ is a radical selected from the group consisting of halogen, $-SCH_3$, $-OH$, alkoxy, cyano, methylamino, carboxy, formyl, nitro and unsubstituted or halosubstituted hydrocarbon groups of 1 through 3 carbon atoms; $R_2$ is hydrogen; halogen or hydroxy; and $R_3$ is hydroxy, $-OP(O)(OH)_2$, amino, or $-OOR_4$ where $R_4$ is lower alkyl of 1 through 6 carbon atoms.

DETAILED DESCRIPTION OF THE INVENTION

As previously discussed, the method of the invention comprises inhibiting the replication of a DNA virus which induces formation of thymidine kinase enzyme, by exposing the virus to an effective concentration of a compound of the formula:

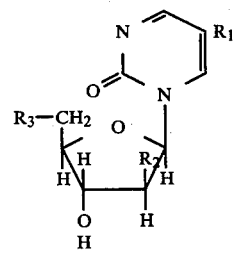

In accordance with the invention, $R_1$ of the formula is a radical selected from the group consisting of halogen, $-SCH_3$, $-OH$, alkoxy, cyano, methylamino, carboxy, formyl, nitro and unsubstituted or halosubstituted hydrocarbon groups of 1 through 3 carbon atoms. The most preferred $R_1$ groups are halogen, cyano, formyl, nitro, alkyl, haloalkyl, alkenyl, haloalkenyl, alkynyl or haloalkynyl groups. Particular compounds which will have good effectiveness are those compounds wherein $R_1$ is selected from methyl, ethynyl, ethyl, propyl, vinyl, halogen, cyano or nitro groups. Such compounds have been unexpectedly found to have superior effectiveness over those compounds wherein $R_1$ is $SCH_3$, $-OH$ or alkoxy. A particularly effective compound having unexpected effectiveness over compounds containing an $R_1$ group which is $SHC_3$, are those compounds wherein $R_1$ is a methyl group.

As previously discussed, $R_2$ is hydrogen, halogen or hydroxy but is preferably hydrogen, fluorine or hydroxy. $R_3$, as previously discussed is hydroxy, $-OP(O)(OH)_2$, amino or $-OOR_4$ where $R_4$ is lower alkyl of 1 through 6 carbon atoms. Preferably, $R_3$ is hydroxy. Compounds wherein $R_3$ is $-OP(O)(OH)_2$, amino or $-OOR_4$, as previously discussed, are generally in themselves, not effective but in In Vivo environments are rapidly converted to compounds wherein $R_3$ is hydroxy.

Examples of compounds suitable for use in accordance with the method of the invention are:
1. 1-(2-Deoxy-beta-D-ribofuranosyl)-5-(methylmercapto)-2-pyrimidinone
2. 1-(2-Deoxy-beta-D-ribofuranosyl)-5-(methyl)-2-pyrimidinone
3. 1-(2-Deoxy-beta-D-ribofuranosyl)-5-(iodo)-2-pyrimidinone
4. 1-(2-Deoxy-beta-D-ribofuranosyl)-5-(trifluoromethyl)-2-pyrimidinone
5. 1-(2-Deoxy-beta-D-ribofuranosyl)-5-(nitro)-2-pyrimidinone
6. 1-(2-Deoxy-beta-D-ribofuranosyl)-5-(cyano)-2-pyrimidinone
7. 1-(2-Deoxy-beta-D-ribofuranosyl)-5-(ethynyl)-2-pyrimidinone
8. 1-(2-Deoxy-beta-D-ribofuranosyl)-5-(propyl)-2-pyrimidinone
9. 1-(2-Deoxy-beta-D-ribofuranosyl)-5-(bromovinyl)-2-pyrimidinone
10. 1-(2-Deoxy-beta-D-ribofuranosyl)-5-(formyl)-2-pyrimidinone
11. 1-(2-Deoxy, 2-fluoro-beta-D-arabinofuranosyl)-5-(methyl)-2-pyrimidinone
12. 1-(beta-D-arabinofuranosyl)-5-(methyl)-2-pyrimidinone An especially effective compound for use in accordance with the present invention is the compound wherein $R_1$ is methyl; $R_2$ is hydrogen and $R_3$ is hydroxy.

In general, such compounds are prepared by reacting a compound of the formula:

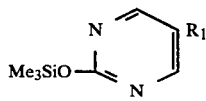

I with a substituted sugar of the formula:

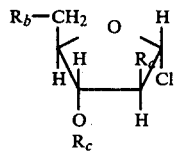

II wherein $R_a$, $R_b$ and $R_c$ are radicals which are non-reactive during the reaction of I with II and which can be converted to the desired $R_2$, $R_3$ and H respectively after reaction of I with II. Detailed discussions of how compounds for use in accordance with the method of the present invention can be prepared are found in Synthesis and Antiviral Activity of 1-(2-Deoxy-beta-D-ribofuranosyl)-5-(methylmercapto)-2-pyrimidinone by Schroeder et al. published in the Journal of Medicinal Chemistry, Volume 24, No. 1, pp 109–112 available to the public Jan. 5, 1981. Further discussion of methods of synthesis of compounds for use in accordance with the method of the present invention is made by Wightman et al, Collection of Czechoslavakian Chemical Communications, Volume 38, beginning at page 1381 (1973) and "Synthesis of New Nucleoside Analogs Derived from 4-oxo Uracil and 6-substituted Uracils" by Schroeder dissertation at the State University of New York at Buffalo (1978).

In accordance with the method of the invention, the replication of numerous viruses can be inhibited. In particular, viruses which induce the formation of thymidine kinase enzyme are inhibited in accordance with the method of the invention. Such viruses generally include essentially all Herpes type Viruses including Herpes simplex 1, Herpes simplex 2, varicella coster, Epstein-bar virus, Cytomegalo virus, varicella zoster, Herpes zoster and variolla. It is known that such viruses cause numerous infections in man including localized infections such as infections of the eye and genitals.

The following examples serve to illustrate and not limit the present invention.

EXAMPLE 1

In accordance with the present invention, 1-(2-Deoxy-beta-D-ribofuranosyl)-5-(methylmercapto)-2-pyrimidinone is prepared essentially in accordance with the procedure set forth in "Synthesis and Antiviral Activity of 1-(2-Deoxy-beta-D-ribofuranosyl)-5-(methylmercapto)-2-pyrimidinone" by Schroeder and Bardos and Cheng, Volume 24, page 109, January 1981. HeLa cells were infected in 1640 RPMI medium with herpes simplex type 1 (HSV-1) and independently with herpes simplex type 2 (HSV-2) virus at a multiplicity of 5 to 10 plaque forming units per cell. The composition of 1640 RPMI medium is reported in "Biological Activity of 5 EThyl, 5 Propyl, and 5 Vinyl 2'-Deoxyuridine" by Cheng et al. published in Antimicrobial Agents Chemotherapy, Volume 10, beginning at page 19 (1976). 1640 RPMI medium is commercially available from Gibco Company, Grand Island, N.Y. After 1 hour, virus absorption, the drugs were added. Resulting cultures were analyzed for virus titer at 24 hours post infection a described in the procedure set forth in "Biological Activity of 5-Ethyl, 5-Propyl and 5-Vinyl 2'-Deoxy uridine" by Cheng et al. The results are set forth in Table 1. The numbers set forth in Table 1 show the number of plaque forming units in the control which contained no methylmercapto compound and the number of units at concentrations of 100, 200 and 400 micromoles of the methylmercapto compound. The results clearly indicate substantial decrease in the number of plaque forming units in the presence of 1-(2-Deoxy-beta-D-ribofuranosyl)-5-(methylmercapto)-2-pyrimidinone.

TABLE 1

| compound conc., $\mu$M | plaque-forming units/mL | |
|---|---|---|
| | HSV-1(Kos) | HSV-2(333) |
| 0 | $1.5 \times 10^7$ | $1.2 \times 10^7$ |
| 100 | $6.4 \times 10^6$ | $1.3 \times 10^7$ |
| 200 | $1.7 \times 10^6$ | $3.1 \times 10^6$ |
| 400 | $3.4 \times 10^5$ | $3.2 \times 10^5$ |

EXAMPLE 2

The methylmercapto composition, as described in Example 1. was tested for binding affinity with thymidine kinase from various sources. Viruses which induce the production of thymidine kinase, induce thymidine kinase specific to the virus. Tests of the binding affinity of the methylmercapto compound with thymidine kinase extracted from human cells showed little binding affinity; whereas, the binding affinity of the methylmercapto compound with thymidine kinase extracted from cells infected with herpes simplex 1 virus and with Varicella zoster virus infected cells, showed great binding affinity. It is believed that the compound of the invention, in order to become active in inhibiting the replication of the virus, must become phosphorylated. For such phosphorylation to occur, the thymidine kinase must first bind to the compound. Since binding with thymidine kinase produced by the virus is much more efficient and effective than binding with thymidine kinase from other sources, phosphorylation of the compound occurs more rapidly in the presence of active viruses producing thymidine kinase. The compound, activated by phosphorylation, then is able to interfere with replication of the virus.

EXAMPLE 3

1-(2-Deoxy-beta-D-ribofuranosyl)-5-(methyl)-2-pyrimidinone, also known as 4-Deoxothymidine, was prepared by thionation of the 4-oxo group of diacetylated thymidine with phosphorus pentasulfide, followed by desulfuration of the 4-thiothymidine derivative by Raney nickel reduction. The method for preparation of the above described methyl compound is essentially the same as described by Wightman et al in Collection of Czechoslavakian Chemical Communications, Volume 38, beginning at page 1381 (1973).

The above described methyl compound was tested for viral inhibition substantially in accordance with the method of Example 1 except that the concentrations were 50 and 100 micromolar. The methyl compound showed a 95.5% inhibition for HSV-1 at 50 micromoles when compared with an untreated control and an 87.9% inhibition for HSV-2 when compared with an untreated control. By comparison, methylmercapato compounds of Example 1 at the same 50 micromolar comcentration showed only a 41.4% inhibition for HSV-1 virus and a 57.2% inhibition for HSV-2 virus. At 100 micromolar concentration, a 99% inhibition was shown for the methyl compound for HSV-1 virus and a 98.3% inhibition was shown for HSV-2 virus. Again, by comparison, the methylmercapato compound of Example 1 only showed a 83.8% inhibition for HSV-1 and a 79.3% inhibition for HSV-2. The dramatically superior inhibition for the methyl compound is unexpected.

What is claimed is:

1. A method for inhibiting the replication of a DNA virus which induces formation of thymidine kinase enzyme, by exposing a susceptible DNA virus to an effective concentration of a compound of the formula:

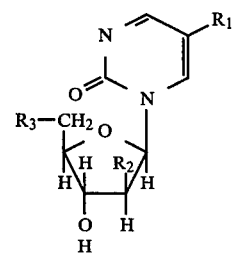

wherein $R_1$ is a radical selected from the group consisting of halogen, $-SCH_3$, $-OH$, alkoxy, cyano, methylamino, carboxy, formyl, nitro and unsubstituted or halosubstituted hydrocarbon groups of 1 through 3 carbon atoms; $R_2$ is hydrogen; halogen or hydroxy; and $R_3$ is hydroxy, $-OP(O)(OH)_2$, amino, or $-OOR_4$ where $R_4$ is lower alkyl of 1 through 6 carbon atoms.

2. The method of claim 1 wherein $R_1$ is a halogen, cyano, formyl, nitro, alkyl, haloalkyl, alkenyl, haloalkenyl, alkynyl or haloalkynyl group of 1 through 3 carbon atoms; $R_2$ is hydrogen, fluorine or hydroxy and $R_3$ is hydroxy.

3. The method of claim 1 wherein the effective concentration is between 25 and 50 micromolar.

4. The method of claim 1 wherein the susceptible DNA virus is located in a warm blooded animal and the effective concentration is obtained in administering from 25 to 1000 milligrams of the compound per kilogram of body weight of the animal.

5. The method of claim 1 wherein $R_1$ is methyl; $R_2$ is hydrogen and $R_3$ is hydroxy.

6. The method of claim 1 wherein the susceptible DNA virus is a Herpes virus.

7. The method of claim 1 wherein $R_1$ is $-SCH_3$, $R_2$ is hydrogen and $R_3$ is hydroxy.

8. The method of claim 1 wherein the compound is 1-(2-Deoxy-beta-D-ribofuranosyl)-5-(iodo)-2-pyrimidinone.

9. The method of claim 2 wherein the compound is 1-(2-Deoxy-beta-D-ribofuranosyl)-5-(ethynyl)-2-pyrimidinone.

* * * * *